(12) United States Patent
McIntyre et al.

(10) Patent No.: US 6,406,908 B1
(45) Date of Patent: *Jun. 18, 2002

(54) VANILLOID RECEPTOR

(75) Inventors: Peter McIntyre; Iain Fraser James, both of London (GB)

(73) Assignee: Novartis AG, Basel (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/533,220

(22) Filed: Mar. 23, 2000

(30) Foreign Application Priority Data

Mar. 26, 1999 (GB) ................................. 0097097

(51) Int. Cl.⁷ ........................... C12N 5/02; C12P 21/06; C07H 21/04
(52) U.S. Cl. ...................... 435/325; 435/69.1; 536/235
(58) Field of Search ................ 435/69.1, 325; 536/23.4

(56) References Cited

U.S. PATENT DOCUMENTS 5,714,666 A * 2/1998 Pritchett et al. ............... 800/2
6,239,267 B1 * 5/2001 Duckworth et al. ....... 536/23.5

FOREIGN PATENT DOCUMENTS

| EP | 0 943 683 A1 | 9/1999 |
| EP | 0 953 638 A1 | 11/1999 |
| WO | WO 99/09140 | 2/1999 |
| WO | WO 00/37765 | 7/1999 |
| WO | WO 99/37675 | 7/1999 |
| WO | WO 99/46377 | 9/1999 |
| WO | WO 00/22121 | 4/2000 |
| WO | WO 00/29577 | 5/2000 |
| WO | WO 00/32766 | 6/2000 |
| WO | WO 00/63415 | 10/2000 |

OTHER PUBLICATIONS

Caterina et al., Nature, vol. 389, "The capsaicin receptor: a heat–activated ion channel in the pain pathway," pp. 816–824 (1997).

Suzuki et al., Journal of Biological Chemistry, vol. 274 (10), "Cloning of a Stretch–inhibitable Nonselective Cation Channel," pp. 6330–6335 (1999).

* cited by examiner

Primary Examiner—Yvonne Eyler
Assistant Examiner—Janet L. Andres
(74) Attorney, Agent, or Firm—Hesna J. Pfeiffer

(57) ABSTRACT

The isolated nucleic acid encoding human vanilloid receptor, said receptor, its preparation, cells expressing said receptor and an assay for testing compounds for their potential to decrease pain in human are disclosed. The receptor is involved in detection of noxious stimuli in mammalian organisms.

4 Claims, No Drawings

VANILLOID RECEPTOR

The present invention is directed to an isolated nucleic acid encoding human vanilloid receptor, said receptor, its preparation, cells expressing said receptor and an assay for testing compounds for their potential to decrease pain in humans.

More particularly the present invention provides in a first aspect, an isolated nucleic acid encoding a human vanilloid receptor.

Even more particularly the present invention provides an isolated nucleic acid capable of directing expression of a human vanilloid receptor, in particular a cDNA capable of directing expression of said receptor, more particularly a cDNA comprising the nucleotide sequence as depicted in SEQ ID NO:1, most particularly a cDNA capable of directing expression of the predicted protein depicted in SEQ ID NO:2.

Said isolated nucleic acid may have a nucleotide sequence having sequence identity within a range of from more than 85.5%, preferably more than 97% to 100% over the open reading frame with the nucleotide sequence as described in SEQ ID NO:1. Preferably said isolated nucleic acid comprises a nucleic acid identical over the open reading frame to the sequence as described in SEQ ID NO:1.

The nucleic acid may be prepared for example by constructing a cDNA library from mRNA derived from human neuronal cells expressing vanilloid receptor. Such cells may be the nociceptive neurones, the cell bodies thereof residing within the dorsal root ganglia. The cDNA may then be expressed in a cell line not normally expressing endogenous vanilloid receptor and by iteratively subdividing and reassaying positive clones an individual clone may be obtained comprising the desired nucleic acid.

In a further embodiment the present invention is directed to a recombinant human vanilloid receptor. An example for said human vanilloid receptor may be a protein encoded by a nucleic acid having sequence identity within a range of from more than 85.5%, preferably more than 97% to 100% over the open reading frame with the nucleotide sequence as described in SEQ ID NO:1, e.g. a protein comprising an amino acid sequence having sequence identity within a range of from more than 85.7% to 100% with the amino acid sequence as described in SEQ ID NO:2, as calculated using the ALIGN program [Myers and Miller, CABIOS (1989)]. The amino acid differences may occur at a site selected from the N-terminus, the C-terminus and the putative pore region of the channel, i.e. amino acid 597 to amino acid 696 of SEQ ID NO:2. Preferably the human vanilloid receptor comprises an amino acid sequence identical to the sequence as described in SEQ ID NO:2.

The human vanilloid receptor when expressed in mammalian cells is activated by capsaicin, temperatures greater than 42° C. and by pH less than 5.5. The activation by all these effectors can be blocked substantially or completely by the action of the capsaicin antagonist capsazepine.

The vanilloid receptor may be prepared by stably transfecting a cell line with an appropriate expression cassette comprising a nucleic acid encoding the receptor, and culturing cells of said cell line under conditions which allow expression of said receptor.

In a further embodiment the present invention is directed to a cell belonging to a cell line expressing recombinant human vanilloid receptor.

In a further embodiment the present invention is directed to a cell belonging to a cell line expressing recombinant mammalian vanilloid receptor and aequorin. Examples for useful cell lines include any cell line growing well in culture, e.g. human embryonic kidney derived cells, like HEK293 cells and Chinese hamster ovary cells, like CHO-DUKX-B11 cells [Kaufman et al., Mol. Cell biol. 5:1750–1759 (1985)], which have been transformed/transfected with an appropriate expression cassette comprising a nucleic acid encoding human or mammalian vanilloid receptor and optionally a nucleic acid encoding aequorin. The expression cassette may be derived from a vector selected from for example pIRESneo, pBKCMV and pXMT3. A very useful cell line is the CHO-DUKX-B11 cell line.

Examples for a mammalian vanilloid receptor are the rat receptor and the human receptor.

Aequorin is a protein from the jellyfish. In the presence of $Ca^{++}$ ions the complex of aequorin and coelenterazine gives off light.

In a further embodiment the present invention is directed to an assay to measure vanilloid receptor activation comprising measuring changes in aequorin luminescence of cells expressing a mammalian vanilloid receptor and aequorin.

In a further embodiment the present invention is directed to a screening assay for vanilloid receptor channel blockers comprising incubation of a cell expressing a mammalian vanilloid receptor and aequorin with the potential vanilloid receptor channel blocker, adding an activator/agonist, e.g. capsaicin, of the vanilloid receptor channel and measuring changes in aequorin luminescence.

In a further embodiment the present invention is directed to a screening assay for vanilloid receptor channel agonists comprising incubation of a cell expressing a mammalian vanilloid receptor and aequorin, adding the potential vanilloid receptor channel agonist and measuring changes in aequorin luminescence.

In a further embodiment the present invention is directed to an assay to measure vanilloid receptor activation comprising measuring changes in the fluorescence of laser activated, calcium sensitive dyes, e.g. fura 2 AM and fluo3.

In a further embodiment the present invention is directed to a screening assay for vanilloid receptor channel blockers comprising incubation of a cell expressing a mammalian vanilloid receptor and optionally aequorin with the potential vanilloid receptor channel blocker, adding an activator/agonist, e.g. capsaicin, of the vanilloid receptor and measuring changes in the fluorescence of laser activated, calcium sensitive dyes, e.g. fura 2 AM and fluo 3.

In a further embodiment the present invention is directed to a screening assay for vanilloid receptor channel agonists comprising incubation of a cell expressing a mammalian vanilloid receptor and optionally aequorin with the potential vanilloid receptor channel agonist and measuring changes in the fluorescence of laser activated, calcium sensitive dyes, e.g. fura 2 AM and fluo3.

The above assay formats allow automation and are suitable for screening.

In a further embodiment the present invention is directed to a novel vanilloid receptor channel blocker identified by a screening assay for vanilloid receptor channel blockers comprising incubation of a cell expressing a mammalian vanilloid receptor and aequorin with the potential vanilloid receptor channel blocker, adding an activator/agonist, e.g. capsaicin, of the vanilloid receptor and measuring changes in aequorin luminescence.

In a further embodiment the present invention is directed to a novel vanilloid receptor channel agonist identified by a screening assay for vanilloid receptor channel agonists comprising incubation of a cell expressing a mammalian vanilloid receptor and aequorin with the potential vanilloid receptor channel agonist and measuring changes in aequorin luminescence.

In a further embodiment the present invention is directed to a novel vanilloid receptor channel blocker identified by a screening assay for vanilloid receptor channel blockers comprising incubation of a cell expressing a mammalian vanilloid receptor and optionally aequorin with the potential vanilloid receptor channel blocker, adding an activator/agonist, e.g. capsaicin, of the vanilloid receptor and measuring changes in the fluorescence of laser activated, calcium sensitive dyes, e.g. fura 2 AM and fluo3.

In a further embodiment the present invention is directed to a novel vanilloid receptor channel agonist identified by a screening assay for vanilloid receptor channel agonists comprising incubation of a cell expressing a mammalian vanilloid receptor and optionally aequorin with the potential vanilloid receptor channel agonist and measuring changes in the fluorescence of laser activated, calcium sensitive dyes, e.g. fura 2 AM and fluo3.

In accordance with the foregoing the present invention also provides:

(1) an isolated nucleic acid encoding a human vanilloid receptor;

(2) a recombinant human vanilloid receptor;

(3) a method of preparation of the receptor of (2);

(4) a cell line expressing the receptor of (2) and optionally aequorin;

(5) an assay to measure vanilloid receptor activation;

(6) a screening assay for vanilloid receptor channel blockers or agonists; and (7) novel vanilloid receptor channel blocker or agonist, e.g. obtained via (6).

The following examples illustrate the invention without limitation. The following abbreviations are used in the examples: DRG: dorsal root ganglion; G418: Geneticin; HBSS: Hanks balanced salt solution; PBS: phosphate buffered saline; RT: room temperature; VR: vanilloid receptor

EXAMPLE A1
Preparation of CHO Cells Expressing Rat VR and Aequorin
(a) Aequorin-pXMT3

The pXMT3 mammalian expression plasmid, SEQ ID NO:3, encodes a cDNA for dihydrofolate reductase. Aequorin-pBk-CMV (SEQ ID NO:4) is linearised with Nhe1 (immediately upstream of the Kozak consensus sequence). The 5' overhang is filled in with Klenow fragment and phosphorylated PstI linker (New England Biolabs) is blunt end ligated to the DNA. The aequorin insert is released with PstI and EcoRI and cloned into pXMT3.

(b) Cloning of rVR1

A rat vanilloid receptor, rVR1, cDNA is cloned by homology cloning from a rat DRG cDNA library in lambda ZAP express using a 969 bp PCR fragment corresponding to nucleotides 1513 to 2482 from the rat VR1 sequence [Caterina et al., Nature 389:816–824 (1997)] as a probe. This probe is derived by RT-PCR using RNA from adult rat DRG [Helliwell et al., Neuroscience Lett. 250:177–180 (1998). The rVR1 insert is then cut out with EcoR1 and Not1 and then subcloned into the pIRESneo expression vector (Accession Number U89673) (Clontech). The rVR1 PCR clone is then subcloned into pcDNA3.1 (Invitrogen) expression vector.

DNA used for transient and stable transfections is purified using Promega's Wizard plus Maxi or Megaprep DNA purification systems.

(c) Production of rVR1/aequorin CHO Cell Stable Clone

DUKX-CHO-Aequorin cells which have previously been transfected with pXMT3-aequorin are transfected with pIRESneo-rVR1 using LipofectAMINE PLUS reagent. 1,000,000 cells are transfected with 1.25 $\mu$g of rVR1 DNA. 2 days following transfectection 700 $\mu$g/ml G418 is used to select for positive cells. Transfected cells are visible after 5 days and continued to be grown in the presence of G418 after that. 10 days later the G418 selected cells are cloned by limiting dilution in 96 well plates and continue to be grown in G418 after that.

EXAMPLE A2
Preparation of CHO Cells Expressing Human VR and Aequorin
(a) Cloning of hVR1

A human DRG cDNA library of approximately 80,000 clones is made in lambda ZAP express using a Stratagene kit. The library is screened at low stringency (2×SSC, 45° C.) using the rat VR1 probe described in Example A1. Several clones are isolated and the longest full-length one, clone 3D, is chosen for expression studies (SEQ ID NO:1). The insert is cut out with Eco R1 and Not 1 and cloned into pIRESneo (Accession Number U89673) (Clontech).

(b) Production of hVR1/Aequorin CHO Cell Stable Clone

DUKX-CHO-Aequorin cells which have previously been transfected with pXMT3-aequorin are transfected with pIRESneo-hVR1 using LipofectAMINE PLUS reagent. 1,000,000 cells are transfected with 1.25 $\mu$g of hVR1 DNA. 2 days following transfection 700 $\mu$g/ml G418 is used to select for positive cells. Transfected cells are visible after 5 days and later, the G418 selected cells are cloned by limiting dilution in 96 well plates and continue to be grown in the presence of G418 after that.

EXAMPLE B1
Potency of Capsaicin (Agonist)
(a) Calcium Uptake Assay

Primary cultures of adult DRG neurones are prepared according to standard protocols [Wood et al., J. Neuroscience 8:3208–3220 (1988)]. Cells are plated at a density of 2000 per well on 96 well view plates pre-coated with poly-ornithine and laminin and cultured in Hams F14 supplemented with 100 ng/ml NGF for four days. On the day of the assay, the cells are washed eight times in a Denley cell washer with calcium/magnesium free HBSS plus 10 mM HEPES, pH7.4. After washing the wells contain approximately 75 $\mu$l of buffer.

To this is added 25 $\mu$l of capsaicin with or without capsazepine or ruthenium red in Ca/Mg free buffer containing 370 KBq of $^{45}Ca^{2+}$/ml. For negative control, capsaicin is omitted. Samples are incubated at RT for 10 min, then washed four times with HBSS/10 mM HEPES pH 7.4. The remaining buffer is removed from the wells and replaced with 25 $\mu$l of 0.1% SDS. After about 10 min 200 $\mu$l of Microscint 40 scintillant is added and samples are counted on a Packard Topcount.

(b) Measurement of Aequorin Activity

Active aequorin is reconstituted by incubating confluent cells resulting from Examples A1 or A2 at 37° C. with 20 $\mu$M coelenterazine h [Biochem. J. 261:913–920 (1989)] and 30 $\mu$M glutathione (reduced form) in 50 $\mu$l of medium per well. All the plates for use in a day are set up at the same time. The first plate is used in the assay after 2.5 h incubation with coelenterazine h. Subsequent plates are used at about 10 min intervals. There is no loss of signal with the longer incubation times. At the start of the assay, the medium containing coelenterazine h is removed and replaced with 100 $\mu$l of HBSS buffered to pH 7.4 with 10 mM HEPES containing test compounds where appropriate. Cells are incubated for at least 10 min at RT. They are then placed in the measuring chamber of a luminometer (Wallac Microbeta Jet). Agonist is injected in a volume of 20 μl HBSS and the luminescence signal is collected for 20 sec.

(c) Fluorometric Assay Using the FLIPR

Cells resulting from Examples A1 or A2 are plated at a density of 50,000 cells/well in Costar Viewplates. The cells are incubated at 37° C. in a humidified atmosphere (5% $CO_2$/95% air) for 24 h. Medium is removed by flicking the plates and replaced with 100 μl HBSS containing 2 μM Fluo-3, AM (Molecular Probes) in the presence of 2.5 mM probenicid (Sigma) and 0.02% pluronic acid (Molecular Probes). The cells are incubated at 37° C. in a humidified atmosphere (5% $CO_2$/95% air) for 1 h. Plates are flicked to remove excess of Fluo-3, AM, washed twice with HBSS and refilled with 100 μl of HBSS containing screening compounds. Incubation in the presence of screening compounds lasts between 10 and 20 min. Plates are then placed in the cell plate stage of the FLIPR (Molecular Devices, Sunnyvale, Calif., USA). A baseline consisting in 5 measurements of 0.4 sec each (laser: excitation 488 nm at 0.6 W, CCD camera opening of 0.4 sec) is recorded. Capsaicin (50 μl at 45 nM) is added from the agonist plate (placed in the agonist plate stage of the FLIPR tower) to the cell plate using the FLIPR 96-tip pipettor simultaneously to fluorescence recording for 3 min according to the following scheme: 0.4 sec measurements each interval of 1 sec for 1 min followed by 0.4 sec measurements each interval of 4 sec for 100 sec. Data are expressed as (Fm-Fb)/Fb where Fm is the fluorescence peak reached following capsaicin injection and Fb is the baseline fluorescence prior to capsaicin injection.

| $EC_{50}$ (nM) (aequorin assay) | $EC_{50}$ (nM) (Ca uptake assay) | $EC_{50}$ (nM) (Fluo-3 assay) |  |
|---|---|---|---|
| rVR1 in CHO cells | hVR1 in CHO cells | Rat DRG neurones | hVR1 in CHO cells |
| 530 ± 110 | 480 ± 64 | 170 ± 19 | 3.42 ± 0.2 |

EXAMPLE B2

Capsazepine and Ruthenium Red Activity on Vanilloid Receptors Activated By Capsaicin (a) Inhibition of capsaicin responses by the competitive antagonist, capsazepine, is measured as described in Example B1. Capsaicin is used at a concentration of 1 μM. The $IC_{50}$ for capsazepine at hVR1 is comparable to that at rVR1 and slightly lower than that measured in calcium uptake assays with DRG neurones.

(b) Activity of the channel blocker ruthenium red is measured as described in Example B1. The layout and conditions are the same as for (a) above. Ruthenium red is an effective blocker of capsaicin responses. The $IC_{50}$ at hVR1 is slightly higher than at the cloned rVR1 or that found in the calcium uptake assay with primary cultures of DRG neurones.

| Compound | $IC_{50}$ (nM) (aequorin assay) | | $IC_{50}$ (nM) (Ca uptake assay) | $IC_{50}$ (nM) |
|---|---|---|---|---|
|  | rVR1 (CHO) | hVR1 (CHO) | Rat DRG neurones | (Fluo-3 assay) hVR1 (CHO) |
| Cz | 320 ± 110 | 120 ± 12 | 800 ± 40 | 130 ± 32 |
| Rr | 18 ± 8.3 | 220 ± 32 | 50* |  |

*From Wood et al (1988)
Cz: Capsazepine; Rr: Ruthenium red; (CHO): in CHO cells

What is claimed is:

1. An isolated nucleic acid encoding a human vanilloid receptor wherein the nucleic acid is cDNA and the cDNA encodes a human vanilloid receptor, the nucleotide sequence of said cDNA has a sequence identity with the nucleotide sequence of SEQ ID NO:1 of from more than 97% to 100%.

2. A cell expressing a recombinant human vanilloid receptor encoded by the nucleotide sequence of claim 1.

3. The cDNA of claim 1 wherein the cDNA comprises a nucleic acid identical over the open reading frame to the sequence as described in SEQ ID NO:1.

4. The cDNA of claim 3 encoding the predicted protein depicted in SEQ ID NO:2.

* * * * *

UNITED STATES PATENT AND TRADEMARK OFFICE
CERTIFICATE OF CORRECTION

PATENT NO.    : 6,406,908 B1
DATED         : June 18, 2002
INVENTOR(S)   : McIntyre et al.

It is certified that error appears in the above-identified patent and that said Letters Patent is hereby corrected as shown below:

<u>Title page,</u>
Item [30], Foreign Application Priority Data, should read:
-- [30]   Foreign Application Priority Data
          Mar. 26, 1999   (GB) ……………………….. 9907097.1 --.

Signed and Sealed this

Twenty-first Day of October, 2003

JAMES E. ROGAN
*Director of the United States Patent and Trademark Office*

SEQUENCE LISTING

<160> NUMBER OF SEQ ID NOS: 4

<210> SEQ ID NO 1
<211> LENGTH: 3463
<212> TYPE: DNA
<213> ORGANISM: Homo sapiens
<220> FEATURE:
<221> NAME/KEY: CDS
<222> LOCATION: (359)..(2875)

<400> SEQUENCE: 1

```
cccccagtt  ttacactttt  acttcccggt  cgtatattgt  gtgaaattgt  g agcggaata      60 cccattttca  cacaaggaac  cagtttatcc  tttgattacg  ccaagctcga  a attaccccc     120 tcattaaaag  ggaacaaaag  ttggagctcg  cgcgcctgca  ggtcgacact  a gtggatcca     180 aagaattcgg  cacgagccgg  gcccgggacc  ccacggaggc  ggggagacca  c tcttctccc     240 acacgagccc  agctctccct  tcgagtagca  accgccttca  agctcacaag  c acccgtggg     300 cctggggtgt  gcctgcgtct  agctggttgc  acactgggcc  acagaggatc  c agcaagg       358
```

```
atg aag aaa tgg agc agc aca gac ttg ggg g ca gct gcg gac cca ctc      406
Met Lys Lys Trp Ser Ser Thr Asp Leu Gly A la Ala Ala Asp Pro Leu
 1               5                  10                 15 caa aag gac acc tgc cca gac ccc ctg gat g ga gac cct aac tcc agg      454
Gln Lys Asp Thr Cys Pro Asp Pro Leu Asp G ly Asp Pro Asn Ser Arg
            20                  25                 30 cca cct cca gcc aag ccc cag ctc tcc acg g cc aag agc cgc acc cgg      502
Pro Pro Pro Ala Lys Pro Gln Leu Ser Thr A la Lys Ser Arg Thr Arg
        35                  40                  45 ctc ttt ggg aag ggt gac tcg gag gag gct t tc ccg gtg gat tgc cct      550
Leu Phe Gly Lys Gly Asp Ser Glu Glu Ala P he Pro Val Asp Cys Pro
    50                  55                  60 cac gag gaa ggt gag ctg gac tcc tgc ccg a cc atc aca gtc agc cct      598
His Glu Glu Gly Glu Leu Asp Ser Cys Pro T hr Ile Thr Val Ser Pro
65                  70                  75                  80 gtt atc acc atc cag agg cca gga gac ggc c cc acc ggt gcc agg ctg      646
Val Ile Thr Ile Gln Arg Pro Gly Asp Gly P ro Thr Gly Ala Arg Leu
                85                  90                  95 ctg tcc cag gac tct gtc gcc gcc agc acc g ag aag acc ctc agg ctc      694
Leu Ser Gln Asp Ser Val Ala Ala Ser Thr G lu Lys Thr Leu Arg Leu
            100                 105                 110 tat gat cgc agg agt atc ttt gaa gcc gtt g ct cag aat aac tgc cag      742
Tyr Asp Arg Arg Ser Ile Phe Glu Ala Val A la Gln Asn Asn Cys Gln
        115                 120                 125 gat ctg gag agc ctg ctc ttc ctg cag a ag agc aag aag cac ctc          790
Asp Leu Glu Ser Leu Leu Phe Leu Gln L ys Ser Lys Lys His Leu
    130                 135                 140 aca gac aac gag ttc aaa gac cct gag aca g gg aag acc tgt ctg ctg      838
Thr Asp Asn Glu Phe Lys Asp Pro Glu Thr G ly Lys Thr Cys Leu Leu
145                 150                 155                 160 aaa gcc atg ctc aac ctg cac gac gga cag a ac acc acc atc ccc ctg      886
Lys Ala Met Leu Asn Leu His Asp Gly Gln A sn Thr Thr Ile Pro Leu
                165                 170                 175 ctc ctg gag atc gcg cgg caa acg gac agc c tg aag gag ctt gtc aac      934
Leu Leu Glu Ile Ala Arg Gln Thr Asp Ser L eu Lys Glu Leu Val Asn
            180                 185                 190 gcc agc tac acg gac agc tac tac aag ggc c ag aca gca ctg cac atc      982
Ala Ser Tyr Thr Asp Ser Tyr Tyr Lys Gly G ln Thr Ala Leu His Ile
        195                 200                 205 gcc atc gag aga cgc aac atg gcc ctg gtg a cc ctc ctg gtg gag aac     1030
Ala Ile Glu Arg Arg Asn Met Ala Leu Val T hr Leu Leu Val Glu Asn
210                 215                 220 gga gca gac gtc cag gct gcg gcc cat ggg g ac ttc ttt aag aaa acc     1078
Gly Ala Asp Val Gln Ala Ala Ala His Gly A sp Phe Phe Lys Lys Thr
225                 230                 235                 240 aaa ggg cgg cct gga ttc tac ttc ggt gaa c tg ccc ctg tcc ctg gcc     1126
Lys Gly Arg Pro Gly Phe Tyr Phe Gly Glu L eu Pro Leu Ser Leu Ala
                245                 250                 255 gcg tgc acc aac cag ctg ggc atc gtg aag t tc ctg ctg cag aac tcc     1174
Ala Cys Thr Asn Gln Leu Gly Ile Val Lys P he Leu Leu Gln Asn Ser
            260                 265                 270 tgg cag acg gcc gac atc agc gcc agg gac t cg gtg ggc aac acg gtg     1222
Trp Gln Thr Ala Asp Ile Ser Ala Arg Asp S er Val Gly Asn Thr Val
        275                 280                 285 ctg cac gcc ctg gtg gag gtg gcc gac aac a cg gcc gac aac acg aag     1270
Leu His Ala Leu Val Glu Val Ala Asp Asn T hr Ala Asp Asn Thr Lys
    290                 295                 300 ttt gtg acg agc atg tac aat gag att ctg a tc ctg ggg gcc aaa ctg     1318
Phe Val Thr Ser Met Tyr Asn Glu Ile Leu I le Leu Gly Ala Lys Leu
```

-continued

```
        305                 310                 315                 320
cac ccg acg ctg aag ctg gag gag ctc acc a ac aag aag gga atg atg        1366
His Pro Thr Leu Lys Leu Glu Glu Leu Thr A sn Lys Lys Gly Met Met
                    325                 330                 335 ccg ctg gct ctg gca gct ggg acc ggg aag a tc ggg gtc ttg gcc tat        1414
Pro Leu Ala Leu Ala Ala Gly Thr Gly Lys I le Gly Val Leu Ala Tyr
                340                 345                 350 att ctc cag cgg gag atc cag gag ccc gag t gc agg cac ctg tcc agg        1462
Ile Leu Gln Arg Glu Ile Gln Glu Pro Glu C ys Arg His Leu Ser Arg
            355                 360                 365 aag ttc acc gag tgg gcc tac ggg ccc gtg c ac tcc tcg ctg tac gac        1510
Lys Phe Thr Glu Trp Ala Tyr Gly Pro Val H is Ser Ser Leu Tyr Asp
        370                 375                 380 ctg tcc tgc atc gac acc tgc gag aag aac t cg gtg ctg gag gtg atc        1558
Leu Ser Cys Ile Asp Thr Cys Glu Lys Asn S er Val Leu Glu Val Ile
385                 390                 395                 400 gcc tac agc agc agc gag acc cct aat cgc c ac gac atg ctc ttg gtg        1606
Ala Tyr Ser Ser Ser Glu Thr Pro Asn Arg H is Asp Met Leu Leu Val
                405                 410                 415 gag ccg ctg aac cga ctc ctg cag gac aag t gg gac aga ttc gtc aag        1654
Glu Pro Leu Asn Arg Leu Leu Gln Asp Lys T rp Asp Arg Phe Val Lys
                420                 425                 430 cgc atc ttc tac ttc aac ttc ctg gtc tac t gc ctg tac atg atc atc        1702
Arg Ile Phe Tyr Phe Asn Phe Leu Val Tyr C ys Leu Tyr Met Ile Ile
            435                 440                 445 ttc acc atg gct gcc tac tac agg ccc gtg g at ggc ttg cct ccc ttt        1750
Phe Thr Met Ala Ala Tyr Tyr Arg Pro Val A sp Gly Leu Pro Pro Phe
        450                 455                 460 aag atg gaa aaa act gga gac tat ttc cga g tt act gga gag atc ctg        1798
Lys Met Glu Lys Thr Gly Asp Tyr Phe Arg V al Thr Gly Glu Ile Leu
465                 470                 475                 480 tct gtg tta gga gga gtc tac ttc ttt ttc c ga ggg att cag tat ttc        1846
Ser Val Leu Gly Gly Val Tyr Phe Phe Phe A rg Gly Ile Gln Tyr Phe
                485                 490                 495 ctg cag agg cgg ccg tcg atg aag acc ctg t tt gtg gac agc tac agt        1894
Leu Gln Arg Arg Pro Ser Met Lys Thr Leu P he Val Asp Ser Tyr Ser
                500                 505                 510 gag atg ctt ttc ttt ctg cag tca ctg ttc a tg ctg gcc acc gtg gtg        1942
Glu Met Leu Phe Phe Leu Gln Ser Leu Phe M et Leu Ala Thr Val Val
            515                 520                 525 ctg tac ttc agc cac ctc aag gag tat gtg g ct tcc atg gta ttc tcc        1990
Leu Tyr Phe Ser His Leu Lys Glu Tyr Val A la Ser Met Val Phe Ser
        530                 535                 540 ctg gcc ttg ggc tgg acc aac atg ctc tac t ac acc cgc ggt ttc cag        2038
Leu Ala Leu Gly Trp Thr Asn Met Leu Tyr T yr Thr Arg Gly Phe Gln
545                 550                 555                 560 cag atg ggc atc tat gcc gtc atg ata gag a ag atg atc ctg aga gac        2086
Gln Met Gly Ile Tyr Ala Val Met Ile Glu L ys Met Ile Leu Arg Asp
                565                 570                 575 ctg tgc cgt ttc atg ttt gtc tac atc gtc t tc ttg ttc ggg ttt tcc        2134
Leu Cys Arg Phe Met Phe Val Tyr Ile Val P he Leu Phe Gly Phe Ser
                580                 585                 590 aca gcg gtg gtg acg ctg att gaa gac ggg a ag aat gac tcc ctg ccg        2182
Thr Ala Val Val Thr Leu Ile Glu Asp Gly L ys Asn Asp Ser Leu Pro
            595                 600                 605 tct gag tcc acg tcg cac agg tgg cgg ggg c ct gcc tgc agg ccc ccc        2230
Ser Glu Ser Thr Ser His Arg Trp Arg Gly P ro Ala Cys Arg Pro Pro
        610                 615                 620 gat agc tcc tac aac agc ctg tac tcc acc t gc ctg gag ctg ttc aag        2278
```

-continued

```
Asp Ser Ser Tyr Asn Ser Leu Tyr Ser Thr Cys Leu Glu Leu Phe Lys
625                 630                 635                 640 ttc acc atc ggc atg ggc gac ctg gag ttc act gag aac tat gac ttc    2326
Phe Thr Ile Gly Met Gly Asp Leu Glu Phe Thr Glu Asn Tyr Asp Phe
                    645                 650                 655 aag gct gtc ttc atc atc ctg ctg gcc tat gta att ctc acc tac        2374
Lys Ala Val Phe Ile Ile Leu Leu Ala Tyr Val Ile Leu Thr Tyr
                660                 665                 670 atc ctc ctg ctc aac atg ctc atc gcc ctc atg ggt gag act gtc aac    2422
Ile Leu Leu Leu Asn Met Leu Ile Ala Leu Met Gly Glu Thr Val Asn
            675                 680                 685 aag atc gca cag gag agc aag aac atc tgg aag ctg cag aga gcc atc    2470
Lys Ile Ala Gln Glu Ser Lys Asn Ile Trp Lys Leu Gln Arg Ala Ile
        690                 695                 700 acc atc ctg gac acg gag aag agc ttc ctt aag tgc atg agg aag gcc    2518
Thr Ile Leu Asp Thr Glu Lys Ser Phe Leu Lys Cys Met Arg Lys Ala
705                 710                 715                 720 ttc cgc tca ggc aag ctg ctg cag gtg ggt tac aca cct gat ggc aag    2566
Phe Arg Ser Gly Lys Leu Leu Gln Val Gly Tyr Thr Pro Asp Gly Lys
                725                 730                 735 gac gac tac cgg tgg tgc ttc agg gtg gac gag gtg aac tgg acc acc    2614
Asp Asp Tyr Arg Trp Cys Phe Arg Val Asp Glu Val Asn Trp Thr Thr
                740                 745                 750 tgg aac acc aac gtg ggc atc atc aac gaa gac ccg ggc aac tgt gag    2662
Trp Asn Thr Asn Val Gly Ile Ile Asn Glu Asp Pro Gly Asn Cys Glu
            755                 760                 765 ggc gtc aag cgc acc ctg agc ttc tcc ctg cgg tca agc aga gtt tca    2710
Gly Val Lys Arg Thr Leu Ser Phe Ser Leu Arg Ser Ser Arg Val Ser
        770                 775                 780 ggc aga cac tgg aag aac ttt gcc ctg gtc ccc ctt tta aga gag gca    2758
Gly Arg His Trp Lys Asn Phe Ala Leu Val Pro Leu Leu Arg Glu Ala
785                 790                 795                 800 agt gct cga gat agg cag tct gct cag ccc gag gaa gtt tat ctg cga    2806
Ser Ala Arg Asp Arg Gln Ser Ala Gln Pro Glu Glu Val Tyr Leu Arg
                805                 810                 815 cag ttt tca ggg tct ctg aag cca gag gac gct gag gtc ttc aag agt    2854
Gln Phe Ser Gly Ser Leu Lys Pro Glu Asp Ala Glu Val Phe Lys Ser
                820                 825                 830 cct gcc gct tcc ggg gag aag tgaggacgtc acgcagac ag cactgtcaac      2905
Pro Ala Ala Ser Gly Glu Lys
835 actgggcctt aggagacccc gttgccacgg ggggctgctg agggaacacc agtgctctgt  2965 cagcagcctg gcctggtctg tgcctgccca gcatgttccc aaatctgtgc tggacaaact  3025 gtgggaaagc gttcttggaa gcatggggag tgatgtacat ccaaccgtca ctgtccccaa  3085 gtgaatctcc taacagactt tcaggttttt actcacttta ctaaacagtg tggatggtca  3145 gtctctactg ggacatgtta ggcccttgtt ttctttgatt ttattctttt ttttgagaca  3205 gaatttcact cttctcgccc aggctggaat gcagtggcac aattttggct cctgcaacc   3265 tccgcctcct ggattccagc aattctcctg cctcggcttc ccaagtagct ggattacag   3325 gcacgtgcca ccatgtctgg ctaattttt ggatttttt aataaaaatg ggggttcgcc    3385 atgttggcca ggctggtctc gaactcctga ccttagggga tccccccacc ttgggcctcc  3445 caaagggctg ggaataca                                                3463
```

<210> SEQ ID NO 2
<211> LENGTH: 839
<212> TYPE: PRT

-continued

```
<213> ORGANISM: Homo sapiens

<400> SEQUENCE: 2

Met Lys Lys Trp Ser Ser Thr Asp Leu Gly Ala Ala Ala Asp Pro Leu
 1               5                  10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
                35                  40                  45

Leu Phe Gly Lys Gly Asp Ser Glu Glu Ala Phe Pro Val Asp Cys Pro
            50                  55                  60

His Glu Glu Gly Glu Leu Asp Ser Cys Pro Thr Ile Thr Val Ser Pro
 65                  70                  75                  80

Val Ile Thr Ile Gln Arg Pro Gly Asp Gly Pro Thr Gly Ala Arg Leu
                    85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
                115                 120                 125

Asp Leu Glu Ser Leu Leu Leu Phe Leu Gln Lys Ser Lys Lys His Leu
                130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                    165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
                195                 200                 205

Ala Ile Glu Arg Arg Asn Met Ala Leu Val Thr Leu Leu Val Glu Asn
                210                 215                 220

Gly Ala Asp Val Gln Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                    245                 250                 255

Ala Cys Thr Asn Gln Leu Gly Ile Val Lys Phe Leu Leu Gln Asn Ser
                260                 265                 270

Trp Gln Thr Ala Asp Ile Ser Ala Arg Asp Ser Val Gly Asn Thr Val
                275                 280                 285

Leu His Ala Leu Val Glu Val Ala Asp Asn Thr Ala Asp Asn Thr Lys
                290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Met
                    325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
                355                 360                 365

Lys Phe Thr Glu Trp Ala Tyr Gly Pro Val His Ser Ser Leu Tyr Asp
                370                 375                 380

Leu Ser Cys Ile Asp Thr Cys Glu Lys Asn Ser Val Leu Glu Val Ile
385                 390                 395                 400
```

-continued

```
Ala Tyr Ser Ser Ser Glu Thr Pro Asn Arg His Asp Met Leu Leu Val
                405                 410                 415
Glu Pro Leu Asn Arg Leu Leu Gln Asp Lys Trp Asp Arg Phe Val Lys
            420                 425                 430
Arg Ile Phe Tyr Phe Asn Phe Leu Val Tyr Cys Leu Tyr Met Ile Ile
        435                 440                 445
Phe Thr Met Ala Ala Tyr Tyr Arg Pro Val Asp Gly Leu Pro Pro Phe
    450                 455                 460
Lys Met Glu Lys Thr Gly Asp Tyr Phe Arg Val Thr Gly Glu Ile Leu
465                 470                 475                 480
Ser Val Leu Gly Gly Val Tyr Phe Phe Arg Gly Ile Gln Tyr Phe
                485                 490                 495
Leu Gln Arg Arg Pro Ser Met Lys Thr Leu Phe Val Asp Ser Tyr Ser
            500                 505                 510
Glu Met Leu Phe Phe Leu Gln Ser Leu Phe Met Leu Ala Thr Val Val
        515                 520                 525
Leu Tyr Phe Ser His Leu Lys Glu Tyr Val Ala Ser Met Val Phe Ser
    530                 535                 540
Leu Ala Leu Gly Trp Thr Asn Met Leu Tyr Tyr Thr Arg Gly Phe Gln
545                 550                 555                 560
Gln Met Gly Ile Tyr Ala Val Met Ile Glu Lys Met Ile Leu Arg Asp
                565                 570                 575
Leu Cys Arg Phe Met Phe Val Tyr Ile Val Phe Leu Phe Gly Phe Ser
            580                 585                 590
Thr Ala Val Val Thr Leu Ile Glu Asp Gly Lys Asn Asp Ser Leu Pro
        595                 600                 605
Ser Glu Ser Thr Ser His Arg Trp Arg Gly Pro Ala Cys Arg Pro Pro
610                 615                 620
Asp Ser Ser Tyr Asn Ser Leu Tyr Ser Thr Cys Leu Glu Leu Phe Lys
625                 630                 635                 640
Phe Thr Ile Gly Met Gly Asp Leu Glu Phe Thr Glu Asn Tyr Asp Phe
                645                 650                 655
Lys Ala Val Phe Ile Ile Leu Leu Leu Ala Tyr Val Ile Leu Thr Tyr
            660                 665                 670
Ile Leu Leu Leu Asn Met Leu Ile Ala Leu Met Gly Glu Thr Val Asn
        675                 680                 685
Lys Ile Ala Gln Glu Ser Lys Asn Ile Trp Lys Leu Gln Arg Ala Ile
    690                 695                 700
Thr Ile Leu Asp Thr Glu Lys Ser Phe Leu Lys Cys Met Arg Lys Ala
705                 710                 715                 720
Phe Arg Ser Gly Lys Leu Leu Gln Val Gly Tyr Thr Pro Asp Gly Lys
                725                 730                 735
Asp Asp Tyr Arg Trp Cys Phe Arg Val Asp Glu Val Asn Trp Thr Thr
            740                 745                 750
Trp Asn Thr Asn Val Gly Ile Ile Asn Glu Asp Pro Gly Asn Cys Glu
        755                 760                 765
Gly Val Lys Arg Thr Leu Ser Phe Ser Leu Arg Ser Ser Arg Val Ser
    770                 775                 780
Gly Arg His Trp Lys Asn Phe Ala Leu Val Pro Leu Leu Arg Glu Ala
785                 790                 795                 800
Ser Ala Arg Asp Arg Gln Ser Ala Gln Pro Glu Glu Val Tyr Leu Arg
                805                 810                 815
Gln Phe Ser Gly Ser Leu Lys Pro Glu Asp Ala Glu Val Phe Lys Ser
```

Pro Ala Ala Ser Gly Glu Lys
835

<210> SEQ ID NO 3
<211> LENGTH: 5155
<212> TYPE: DNA
<213> ORGANISM: Homo sapiens

<400> SEQUENCE: 3

| | | | | | |
|---|---|---|---|---|---|
| aagctttttg | caaaagccta | ggaaaaaagc | ctcctcacta | cttctggaat a | gctcagagg 60 |
| ccgaggcggc | ctcggcctct | gcataaataa | aaaaaattag | tcagccatgg g | gcggagaat 120 |
| gggcggaact | gggcggagtt | aggggcggga | tgggcggagt | tagggggcggg a | ctatggttg 180 |
| ctgactaatt | gagatgcatg | ctttgcatac | ttctgcctgc | tggggagcct g | ggactttc 240 |
| cacacctggt | tgctgactaa | ttgagatgca | tgctttgcat | acttctgcct g | ctggggagc 300 |
| ctggggactt | tccacaccct | aactgacaca | cattccacag | gatccggtcg c | gcgaatttc 360 |
| gagcggtgtt | ccgcggtcct | cctcgtatag | aaactcggac | cactctgaga c | gaaggctcg 420 |
| cgtccaggcc | agcacgaagg | aggctaagtg | ggaggggtag | cggtcgttgt c | cactagggg 480 |
| gtccactcgc | tccagggtgt | gaagacacat | gtcgccctct | tcggcatcaa g | gaaggtgat 540 |
| tggtttatag | gtgtaggcca | cgtgaccggg | tgttcctgaa | gggggggctat a | aaagggggt 600 |
| gggggcgcgt | tcgtcctcac | tctcttccgc | atcgctgtct | gcgagggcca g | ctgttgggc 660 |
| tcgcggttga | ggacaaactc | ttcgcggtct | ttccagtact | cttggatcgg a | acccgtcg 720 |
| gcctccgaac | ggtactccgc | caccgaggga | cctgagcgag | tccgcatcga c | cggatcgga 780 |
| aaacctctcg | actgttgggg | tgagtactcc | ctctcaaaag | cgggcatgac t | tctgcgcta 840 |
| agattgtcag | tttccaaaaa | cgaggaggat | ttgatattca | cctggcccgc g | gtgatgcct 900 |
| ttgagggtgg | ccgcgtccat | ctggtcagaa | aagacaatct | ttttgttgtc a | gcttgagg 960 |
| tgtggcaggc | ttgagatctg | gccatacact | tgagtgacaa | tgacatccac t | ttgccttc 1020 |
| tctccacagg | tgtccactcc | caggtccaac | tgcaggtcga | ctctagagga t | ccccgggta 1080 |
| ccgagctcga | attccggggg | ggggggggg | gggacagct | cagggctgcg a | tttcgcgcc 1140 |
| aaacttgacg | gcaatcctag | cgtgaaggct | ggtaggattt | tatccccgct g | ccatcatgg 1200 |
| ttcgaccatt | gaactgcatc | gtcgccgtgt | cccaaaatat | ggggattggc a | gaacggag 1260 |
| acctaccctg | gcctccgctc | aggaacgagt | tcaagtactt | ccaaagaatg a | ccacaacct 1320 |
| cttcagtgga | aggtaaacag | aatctggtga | ttatgggtag | gaaaacctgg t | tctccattc 1380 |
| ctgagaagaa | tcgaccttta | aaggacagaa | ttaatatagt | tctcagtaga g | aactcaaag 1440 |
| aaccaccacg | aggagctcat | tttcttgcca | aaagtttgga | tgatgcctta a | gacttattg 1500 |
| aacaaccgga | attggcaagt | aaagtagaca | tggtttggat | agtcggaggc a | gttctgttt 1560 |
| accaggaagc | catgaatcaa | ccaggccacc | tcagactctt | tgtgacaagg a | tcatgcagg 1620 |
| aatttgaaag | tgacacgttt | ttcccagaaa | ttgatttggg | gaaatataaa c | ttctcccag 1680 |
| aatacccagg | cgtcctctct | gaggtccagg | aggaaaaagg | catcaagtat a | agtttgaag 1740 |
| tctacgagaa | gaaagactaa | caggaagatg | ctttcaagtt | ctctgctccc c | tcctaaagc 1800 |
| tatgcatttt | ttataagacc | atgggacttt | tgctggcttt | agatcataat c | agccatacc 1860 |
| acatttgtag | aggttttact | tgctttaaaa | aacctcccac | acctccccct g | aacctgaaa 1920 |
| cataaaatga | atgcaattgt | tgttgttaac | ttgtttattg | cagcttataa t | ggttacaaa 1980 |

-continued

| | | | | |
|---|---|---|---|---|
| taaagcaata | gcatcacaaa | tttcacaaat | aaagcatttt | tttcactgca t tctagttgt | 2040 |
| ggtttgtcca | aactcatcaa | tgtatcttat | catgtctgga | tccccggcca a cggtctggt | 2100 |
| gacccggctg | cgagagctcg | gtgtacctga | gacgcgagta | agcccttgag t caaagacgt | 2160 |
| agtcgttgca | agtccgcacc | aggtactgat | atcccaccaa | aaagtgcggc g gcggctggc | 2220 |
| ggtagagggg | ccagcgtagg | gtggccgggg | ctccgggggc | gaggtcttcc a acataaggc | 2280 |
| gatgatatcc | gtagatgtac | ctggacatcc | aggtgatgcc | ggcggcggtg g tggaggcgc | 2340 |
| gcggaaagtc | gcggacgcgg | ttccagatgt | tgcgcagcgg | caaaaagtgc t ccatggtcg | 2400 |
| ggacgctctg | gccggtgagg | cgtgcgcagt | cgttgacgct | ctagaccgtg c aaaaggaga | 2460 |
| gcctgtaagc | gggcactctt | ccgtggtctg | gtggataaat | tcgcaagggt a tcatggcgg | 2520 |
| acgaccgggg | ttcgaacccc | ggatccggcc | gtccgccgtg | atccatccgg t taccgcccg | 2580 |
| cgtgtcgaac | ccaggtgtgc | gacgtcagac | aacgggggag | cgctccttt g gcttccttc | 2640 |
| caggcgcggc | ggctgctgcg | ctagcttttt | tggcgagctc | gaattaattc t gcattaatg | 2700 |
| aatcggccaa | cgcgcgggga | gaggcggttt | gcgtattggg | cgctcttccg c ttcctcgct | 2760 |
| cactgactcg | ctgcgctcgg | tcgttcggct | gcggcgagcg | gtatcagctc a ctcaaaggc | 2820 |
| ggtaatacgg | ttatccacag | aatcagggga | taacgcagga | aagaacatgt g agcaaaagg | 2880 |
| ccagcaaaag | gccaggaacc | gtaaaaaggc | cgcgttgctg | gcgtttttcc a taggctccg | 2940 |
| cccccctgac | gagcatcaca | aaaatcgacg | ctcaagtcag | aggtggcgaa a cccgacagg | 3000 |
| actataaaga | taccaggcgt | ttccccctgg | aagctccctc | gtgcgctctc c tgttccgac | 3060 |
| cctgccgctt | accggatacc | tgtccgcctt | tctcccttcg | ggaagcgtgg c gctttctca | 3120 |
| atgctcacgc | tgtaggtatc | tcagttcggt | gtaggtcgtt | cgctccaagc t gggctgtgt | 3180 |
| gcacgaaccc | cccgttcagc | ccgaccgctg | cgccttatcc | ggtaactatc g tcttgagtc | 3240 |
| caacccggta | agacacgact | tatcgccact | ggcagcagcc | actggtaaca g gattagcag | 3300 |
| agcgaggtat | gtaggcggtg | ctacagagtt | cttgaagtgg | tggcctaact a cggctacac | 3360 |
| tagaaggaca | gtatttggta | tctgcgctct | gctgaagcca | gttaccttcg g aaaaagagt | 3420 |
| tggtagctct | tgatccggca | aacaaaccac | cgctggtagc | ggtggttttt t tgtttgcaa | 3480 |
| gcagcagatt | acgcgcagaa | aaaaaggatc | tcaagaagat | cctttgatct t ttctacggg | 3540 |
| gtctgacgct | cagtggaacg | aaaactcacg | ttaagggatt | ttggtcatga g attatcaaa | 3600 |
| aaggatcttc | acctagatcc | ttttaaatta | aaaatgaagt | tttaaatcaa t ctaaagtat | 3660 |
| atatgagtaa | acttggtctg | acagttacca | atgcttaatc | agtgaggcac c tatctcagc | 3720 |
| gatctgtcta | tttcgttcat | ccatagttgc | ctgactcccc | gtcgtgtaga t aactacgat | 3780 |
| acgggagggc | ttaccatctg | gccccagtgc | tgcaatgata | ccgcgagacc c acgctcacc | 3840 |
| ggctccagat | ttatcagcaa | taaaccagcc | agccggaagg | gccgagcgca g aagtggtcc | 3900 |
| tgcaacttta | tccgcctcca | tccagtctat | taattgttgc | cgggaagcta g agtaagtag | 3960 |
| ttcgccagtt | aatagtttgc | gcaacgttgt | tgccattgct | acaggcatcg t ggtgtcacg | 4020 |
| ctcgtcgttt | ggtatggctt | cattcagctc | cggttcccaa | cgatcaaggc g agttacatg | 4080 |
| atcccccatg | ttgtgcaaaa | aagcggttag | ctccttcggt | cctccgatcg t tgtcagaag | 4140 |
| taagttggcc | gcagtgttat | cactcatggt | tatggcagca | ctgcataatt c tcttactgt | 4200 |
| catgccatcc | gtaagatgct | tttctgtgac | tggtgagtac | tcaaccaagt c attctgaga | 4260 |
| atagtgtatg | cggcgaccga | gttgctcttg | cccggcgtca | atacgggata a taccgcgcc | 4320 |
| acatagcaga | actttaaaag | tgctcatcat | tggaaaacgt | tcttcggggc g aaaactctc | 4380 |

```
aaggatctta ccgctgttga gatccagttc gatgtaaccc actcgtgcac c caactgatc    4440 ttcagcatct tttactttca ccagcgtttc tgggtgagca aaaacaggaa g gcaaaatgc    4500 cgcaaaaaag ggaataaggg cgacacggaa atgttgaata ctcatactct t cctttttca    4560 atattattga agcatttatc agggttattg tctcatgagc ggatacatat t tgaatgtat    4620 ttagaaaaat aaacaaatag gggttccgcg cacatttccc cgaaaagtgc c acctgacgt    4680 ctaagaaacc attattatca tgacattaac ctataaaaat aggcgtatca c gaggccctt    4740 tcgtctcgcg cgtttcggtg atgacggtga aaacctctga cacatgcagc t cccggagac    4800 ggtcacagct tgtctgtaag cggatgccgg gagcagacaa gcccgtcagg g cgcgtcagc    4860 gggtgttggc gggtgtcggg gctggcttaa ctatgcggca tcagagcaga t tgtactgag    4920 agtgcaccat atgcggtgcg aaataccgca cagatgcgta aggagaaaat a ccgcatcag    4980 gcgccattcg ccattcaggc tgcgcaactg ttgggaaggg cgatcggtgc g ggcctcttc    5040 gctattacgc cagctggcga aaggggatg tgctgcaagg cgattaagtt g ggtaacgcc    5100 aggttttcc cagtcacgac gttgtaaaac gacggccagt gccaagcttt t tgca         5155

<210> SEQ ID NO 4
<211> LENGTH: 4886
<212> TYPE: DNA
<213> ORGANISM: Homo sapiens

<400> SEQUENCE: 4
ctagcatgca gtcaagctta catcagactt cgacaaccca agatggattg g acgacacaa      60 gcatatgttc aatttccttg atgtcaacca caatggaaaa atctctcttg a cgagatggt     120 ctacaaggca tctgatattg tcatcaataa ccttggagca acacctgagc a agccaaacg     180 acacaaagat gctgtagaag ccttcttcgg aggagctgga atgaaatatg g tgtggaaac     240 tgattggcct gcatatattg aaggatggaa aaaattggct actgatgaat t ggagaaata     300 cgccaaaaac gaaccaacgc tcatccgtat atggggtgat gctttgtttg a tatcgttga     360 caaagatcaa aatggagcca ttacactgga tgaatggaaa gcatacacca a agctgctgg     420 tatcatccaa tcatcagaag attgcgagga acattcaga gtgtgcgata t tgatgaaag     480 tggacaactc gatgttgatg agatgacaag acaacattta ggattttggt a caccatgga     540 tcctgcttgc gaaaagctct acggtggagc tgtcccctaa gaagaattca a aaagcttct     600 cgagagtact tctagagcgg ccgcgggccc atcgattttc cacccgggtg g ggtaccagg     660 taagtgtacc caattcgccc tatagtgagt cgtattacaa ttcactggcc g tcgttttac     720 aacgtcgtga ctgggaaaac cctggcgtta cccaacttaa tcgccttgca g cacatcccc     780 ctttcgccag ctggcgtaat agcgaagagg cccgcaccga tcgcccttcc c aacagttgc     840 gcagcctgaa tggcgaatgg agatccaatt tttaagtgta taatgtgtta a actactgat     900 tctaattgtt tgtgtatttt agattcacag tcccaaggct catttcaggc c cctcagtcc     960 tcacagtctg ttcatgatca taatcagcca taccacattt gtagaggttt t acttgcttt    1020 aaaaaacctc ccacacctcc ccctgaacct gaaacataaa atgaatgcaa t tgttgttgt    1080 taacttgttt attgcagctt ataatggtta caaataaagc aatagcatca c aaatttcac    1140 aaataaagca ttttttcac tgcattctag ttgtggtttg tccaaactca t caatgtatc    1200 ttaacgcgta aattgtaagc gttaatattt tgttaaaatt cgcgttaaat t tttgttaaa    1260 tcagctcatt ttttaaccaa taggccgaaa tcggcaaaat cccttataaa t caaaagaat    1320
```

-continued

```
agaccgagat agggttgagt gttgttccag tttggaacaa gagtccacta t taaagaacg    1380 tggactccaa cgtcaaaggg cgaaaaaccg tctatcaggg cgatggccca c tacgtgaac    1440 catcacccta atcaagtttt tgggtcga ggtgccgtaa agcactaaat c ggaaccta     1500 aagggagccc ccgatttaga gcttgacggg gaaagccggc gaacgtggcg a gaaggaag    1560 ggaagaaagc gaaaggagcg ggcgctaggg cgctggcaag tgtagcggtc a cgctgcgcg   1620 taaccaccac acccgccgcg cttaatgcgc cgctacaggg cgcgtcaggt g cactttc     1680 ggggaaatgt gcgcggaacc cctatttgtt tattttcta aatacattca a atatgtatc    1740 cgctcatgag acaataaccc tgataaatgc ttcaataata ttgaaaaagg a gagtcctg    1800 aggcggaaag aaccagctgt ggaatgtgtg tcagttaggg tgtggaaagt c cccaggctc   1860 cccagcaggc agaagtatgc aaagcatgca tctcaattag tcagcaacca g gtgtggaaa   1920 gtccccaggc tccccagcag gcagaagtat gcaaagcatg catctcaatt a gtcagcaac   1980 catagtcccg ccctaactc cgcccatccc gcccctaact ccgcccagtt c cgcccattc    2040 tccgccccat ggctgactaa ttttttttat ttatgcagag gccgaggccg c ctcggcctc   2100 tgagctattc cagaagtagt gaggaggctt ttttggaggc ctaggctttt g caaagatcg   2160 atcaagagac aggatgagga tcgtttcgca tgattgaaca agatggattg c acgcaggtt   2220 ctccggccgc ttgggtggag aggctattcg gctatgactg ggcacaacag a caatcggct   2280 gctctgatgc cgccgtgttc cggctgtcag cgcaggggcg cccggttctt t ttgtcaaga   2340 ccgacctgtc cggtgccctg aatgaactgc aagacgagga agcgcggcta t cgtggctgg   2400 ccacgacggg cgttccttgc gcagctgtgc tcgacgttgt cactgaagcg g aagggact   2460 ggctgctatt gggcgaagtg ccggggcagg atctcctgtc atctcaccttg ctcctgccg    2520 agaaagtatc catcatggct gatgcaatgc ggcggctgca tacgcttgat c cggctacct   2580 gcccattcga ccaccaagcg aaacatcgca tcgagcgagc acgtactcgg a tggaagccg   2640 gtcttgtcga tcaggatgat ctggacgaag agcatcaggg gctcgcgcca g ccgaactgt   2700 tcgccaggct caaggcgagc atgcccgacg gcgaggatct cgtcgtgacc c atggcgatg   2760 cctgcttgcc gaatatcatg gtggaaaatg gccgcttttc tggattcatc g actgtggcc   2820 ggctgggtgt ggcggaccgc tatcaggaca tagcgttggc tacccgtgat a ttgctgaag   2880 agcttggcgg cgaatgggct gaccgcttcc tcgtgcttta cggtatcgcc g ctcccgatt   2940 cgcagcgcat cgccttctat cgccttcttg acgagttctt ctgagcggga c tctgggtt    3000 cgaaatgacc gaccaagcga cgcccaacct gccatcacga gatttcgatt c caccgccgc   3060 cttctatgaa aggttgggct tcggaatcgt tttccgggac gccggctgga t gatcctcca   3120 gcgcggggat ctcatgctgg agttcttcgc ccaccctagg gggaggctaa c tgaaacacg   3180 gaaggagaca ataccggaag gaacccgcgc tatgacggca ataaaaagac a gaataaaac   3240 gcacggtgtt gggtcgtttg ttcataaacg cggggttcgg tcccagggct g cactctgt    3300 cgatacccca ccgagacccc attggggcca atacgcccgc gtttcttcct t tcccccacc   3360 ccaccccca agttcgggtg aaggcccagg gctcgcagcc aacgtcgggg c gcaggccc    3420 tgccatagcc tcaggttact catatatact ttagattgat ttaaaacttc a tttttaatt   3480 taaaaggatc taggtgaaga tccttttga taatctcatg accaaaatcc c ttaacgtga    3540 gttttcgttc cactgagcgt cagacccocgt agaaaagatc aaaggatctt c ttgagatcc   3600 ttttttttctg cgcgtaatct gctgcttgca acaaaaaaa ccaccgctac c agcggtggt   3660 ttgtttgccg gatcaagagc taccaactct ttttccgaag gtaactggct t cagcagagc   3720
```

-continued

```
gcagatacca aatactgtcc ttctagtgta gccgtagtta ggccaccact t caagaactc    3780
tgtagcaccg cctacatacc tcgctctgct aatcctgtta ccagtggctg c tgccagtgg    3840
cgataagtcg tgtcttaccg ggttggactc aagacgatag ttaccggata a ggcgcagcg    3900
gtcgggctga acgggggggtt cgtgcacaca gcccagcttg gagcgaacga c ctacaccga   3960
actgagatac ctacagcgtg agctatgaga aagcgccacg cttcccgaag g gagaaaggc    4020
ggacaggtat ccggtaagcg gcagggtcgg aacaggagag cgcacgaggg a gcttccagg    4080
gggaaacgcc tggtatcttt atagtcctgt cgggtttcgc cacctctgac t tgagcgtcg    4140
atttttgtga tgctcgtcag gggggcggag cctatggaaa aacgccagca a cgcggcctt    4200
tttacggttc ctggcctttt gctggccttt tgctcacatg ttctttcctg c gttatcccc    4260
tgattctgtg gataaccgta ttaccgccat gcattagtta ttaatagtaa t caattacgg    4320
ggtcattagt tcatagccca tatatggagt tccgcgttac ataacttacg g taaatggcc    4380
cgcctggctg accgcccaac gaccccgcc cattgacgtc aataatgacg t atgttccca    4440
tagtaacgcc aatagggact ttccattgac gtcaatgggt ggagtattta c ggtaaactg    4500
cccacttggc agtacatcaa gtgtatcata tgccaagtac gccccctatt g acgtcaatg    4560
acggtaaatg gcccgcctgg cattatgccc agtacatgac cttatgggac t ttcctactt    4620
ggcagtacat ctacgtatta gtcatcgcta ttaccatggt gatgcggttt t ggcagtaca    4680
tcaatgggcg tggatagcgg tttgactcac ggggatttcc aagtctccac c ccattgacg    4740
tcaatgggag tttgttttgg caccaaaatc aacgggactt tccaaaatgt c gtaacaact    4800
ccgccccatt gacgcaaatg ggcggtaggc gtgtacggtg ggaggtctat a taagcagag    4860
ctggtttagt gaaccgtcag atccga                                         4886
```